United States Patent [19]

Cottman

[11] 4,108,831

[45] Aug. 22, 1978

[54] HYDROXYALKYLTHIO PHENOLIC ANTIOXIDANTS

[75] Inventor: Kirkwood S. Cottman, Akron, Ohio

[73] Assignee: The Goodyear Tire & Rubber Company, Akron, Ohio

[21] Appl. No.: 583,064

[22] Filed: Jun. 2, 1975

[51] Int. Cl.$^2$ .................... C08K 5/36; C07C 149/36
[52] U.S. Cl. .................... 260/45.95 C; 260/609 F
[58] Field of Search ............ 260/45.95 C, 609 D, 260/609 F

[56] References Cited

U.S. PATENT DOCUMENTS

| | | | |
|---|---|---|---|
| 2,417,118 | 3/1947 | McCleary et al. | 260/45.95 C |
| 2,549,118 | 4/1951 | Newby | 260/45.95 C |
| 3,260,757 | 7/1966 | O'Shea | 260/45.95 C |
| 3,346,648 | 10/1967 | Worrel | 260/45.95 C |
| 3,553,163 | 1/1971 | Spacht | 260/609 F |
| 3,590,085 | 6/1971 | Braus et al. | 260/45.95 C |
| 3,646,220 | 2/1972 | Dachs et al. | 260/609 D |
| 3,751,483 | 8/1973 | Cisney | 260/45.95 C |

FOREIGN PATENT DOCUMENTS 49-61131  6/1974  Japan.
49-75550  7/1974  Japan.

*Primary Examiner*—V. P. Hoke
*Attorney, Agent, or Firm*—J. A. Rozmajzl

[57] ABSTRACT

Hydroxyalkylthio phenols such as 2,6-ditertiary butyl-4-(2-hydroxyethylthio)phenol used as antioxidants to stabilize polymers against oxidative degradation.

9 Claims, No Drawings

HYDROXYALKYLTHIO PHENOLIC ANTIOXIDANTS

This invention relates to hydroxyalkylthio phenolic antioxidants.

U.S. Pat. No. 3,553,163 reveals ring substituted alkylthio phenolic antioxidants. U.S. Pat. No. 3,565,857 reveals alkylthio substituted polynuclear phenolic antioxidants. Canadian Patent No. 1,290,132 reveals the preparation of ring substituted mercaptophenols. U.S. Pat. No. 3,751,483 reveals the preparation of phenolic thioethers. Those skilled in the art are constantly searching for new antioxidant systems.

It is an object of the present invention to provide new antioxidants for the stabilization of polymers and other materials subject to oxidative degradation as well as to provide stabilized polymers. It is also an object of the present invention to provide the art with a novel method of preparing said antioxidants. Further objects will become apparent as the description of the present invention proceeds.

The objects of the present invention are accomplished by the preparation and use as an antioxidant of a compound conforming to the following structural formula

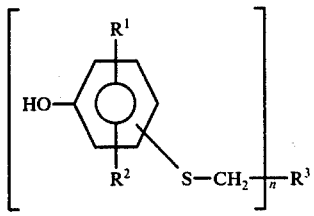

wherein $R^1$ and $R^2$ are selected from the group consisting of hydrogen and hydrocarbon radicals containing 1 to 12 carbon atoms, $R^3$ is a monohydroxy or dihydroxy substituted radical containing 1 to 11 carbon atoms, at least one carbon atom of which is non-aromatic, more particularly a part of a non-cyclic (open chain) aliphatic radical. The non-aromatic portion of $R^3$ contains the hydroxy substitution with the proviso that when $R^3$ contains 2 hydroxy substituents the substituents are located on different carbon atoms, wherein $n$ is 1 or 2 and wherein the thio radical is attached to the phenolic ring in a position ortho or para to the hydroxy group, with the further proviso that when $n$ is 1, $R^3$ is a saturated or unsaturated hydrocarbon radical and when $n$ is 2, $R^3$ is a saturated hydrocarbon radical which can contain 1 or 2 oxyether linkages, i.e., —O—.

A preferred embodiment includes those compounds wherein $R^1$ and $R^2$ are hydrogen or tertiary alkyl radicals having 4 to 9 carbon atoms and are located in the positions ortho to the hydroxy group, and wherein the thio group or groups are in positions para to the hydroxy groups, and wherein $n$ is 1 and $R^3$ has the structural formula $$-\text{CH}-R^4$$
$$|$$
$$\text{OH}$$

wherein $R^4$ is selected from the group consisting of hydrogen, methyl or phenyl and wherein $n$ is 2 and $R^3$ is the group $$-\text{CH}-$$
$$|$$
$$\text{OH}$$

The following compounds illustrate, but do not limit, the antioxidants of the present invention.

2,6-ditertiary butyl-4-(2-hydroxyethylthio)phenol
2-(hydroxyethylthio)phenol
2,6-ditertiary butyl-4-(2-hydroxypropylthio)phenol
2,6-ditertiary butyl-4-(1-methyl-2-hydroxyethylthio) phenol
2,6-ditertiary amyl-4-(4-hydroxybutylthio)phenol
2-tertiary butyl-4-methyl-6-(2-hydroxyethylthio)phenol
2-tertiary butyl-4-(2-hydroxypropyl)phenol
2,6-ditertiary butyl-4-(10-hydroxydecylthio)phenol
2-(α-phenylethyl)-4-(2-hydroxypropylthio)phenol
2,6-ditertiary butyl-4-(2-hydroxy-2-phenylethylthio) phenol
2,6-ditertiary butyl-4-(6-hydroxyhexylthio)phenol
1,3-bis(3,5-ditertiary butyl-4-hydroxyphenylthio)-2-hydroxypropane
1,3-bis(4-hydroxyphenylthio)-2-hydroxypropane
1,4-bis[3-(3,5-ditertiary butyl-4-hydroxyphenylthio)-2-hydroxypropoxy]butane
1,3-bis(3,5-ditertiary hexyl-4-hydroxyphenylthio)-2-hydroxypropane
1,4-bis[3,5-ditertiary butyl-4-hydroxyphenylthio)-2,3-dihydroxy]butane
1,4-bis[2-(3,5-ditertiary butyl-4-hydroxyphenylthio)-1-hydroxyethyl]benzene The addition of hydrocarbon groups to the phenolic ring results in increased solubility in rubber and decreased volatility.

The compounds of this invention may have varying solubility in different solvents depending on their polarity. For example, 2-hydroxyethylthio phenol is very soluble in polar solvents such as methanol, tetrahydrofuran and water. It has limited solubility in aromatic solvents such as benzene and toluene. The similar butylated derivative, 2,6-ditertiary butyl-4-(2-hydroxyethylthio)phenol is less polar because of the butyl groups. It is soluble in aromatic solvents such as benzene, toluene and xylene. It is not soluble in water. Solubility should be considered when one of the compounds is being added to a solution of a polymer. It also follows that a highly polar compound may have a more limited solubility in polymers per se.

Generally the compounds of this invention may be prepared from epoxides such as styrene oxide, ethylene oxide and propylene oxide. The reaction may be carried out using no catalyst or in the presence of basic catalyst such as NaOH or KOH. It may also be carried out in the presence of acidic catalyst such as toluene sulfonic acid. The reaction between 4-(mercapto)phenol and propylene oxide works well using no catalyst, KOH or toluene sulfonic acid. One should consider the stability of the epoxide when choosing a catalyst. For example, some epoxides may give less side reactions in basic media than in acid media. Reactions involving epoxides should be carried out above the polymerization temperature of the epoxide and below the boiling point of the thiol reactant. Temperatures from 90° C. to 155° C. are usually adequate. It may also be advantageous to run the reaction under slight pressure. Usually solvents are not needed when the products are formed by using epoxides. However aromatic solvents such as toluene and xylene may be used.

The compounds of the invention may also be prepared by reacting the basic salt of a (thiol) phenol with a reactive halogen containing alcohol. The (thiol) phenol is treated with a base to form the salt, which is then reacted with the reactive halogen containing alcohol. For example, in preparing 2,6-ditertiary butyl-4-(2-hydroxyethylthio) phenol, one mole of KOH is reacted with the thio group in one mole of 2,6-ditertiary butyl-4-(thio)phenol. One mole of 2-chloroethanol is then added.

Solvents for reactions of this type may be polar solvents such as ethanol, dioxane, and tetrahydrofuran. Aromatic solvents such as benzene, toluene and xylene may be used. Aliphatic hydrocarbon solvents may be used where solubility is not a problem. A combination of aromatic and polar solvents is preferred in most instances.

Reaction temperatures from 25° C. to 100° C. are usually adequate.

None of the aforementioned process information is meant to be critical to the practice of the present invention. The compounds will be effective as antioxidants regardless of their method of preparation.

The following examples illustrate, but do not limit, the preparation of the phenolic compounds of the present invention.

EXAMPLE I

Preparation of 4-(2-hydroxy-2-phenylethylthio)phenol

4-Mercaptophenol (63 grams) and 0.5 gram of KOH were combined in a flask equipped with an agitator, water condenser and thermometer. The combination was heated to 120° C. under nitrogen. Styrene oxide (66 grams) was added dropwise at 100° C. to 135° C. The combination was neutralized with one millimeter of hydrochloric acid and the volatiles stripped off to a pot temperature of 170° C. at 28 millimeters of mercury. The weight of product was 131 grams.

EXAMPLE II

Preparation of 2,6-ditertiary butyl-4-(hydroxyethylthio)phenol

Using the equipment described in Example I, 2,6-ditertiary butyl-4-mercaptophenol (50 grams) was dissolved in 90 millimeters of ethanol (denatured alcohol) and 30 millimeters of benzene. A solution of 12 grams of KOH in 60 millimeters of ethanol was added under a nitrogen blanket. 2-Chloroethanol (19 grams) was slowly added dropwise at room temperature. The combination was reacted for three hours and then diluted with benzene and washed with water. The volatiles were then stripped off.

EXAMPLE III

Preparation of 4-(2-hydroxyethylthio)phenol

4-Mercaptophenol (126 grams) was dissolved in 60 millimeters of ethanol. A solution of KOH (58 grams) dissolved in ethanol (150 millimeters) was added under a nitrogen blanket. 2-Chloroethanol (83 grams) was then added slowly and the combination allowed to react for 1½ hours. The product was filtered and the volatiles stripped off. The weight of product was 172 grams.

EXAMPLE IV

Preparation of 1,3-bis-(3,5-ditertiary-4-hydroxyphenylthio)-2-hydroxypropane 2,6-Ditertiary butyl-4-(thio)phenol (100 grams) and potassium hydroxide (1.0 gram) were combined. The system was purged with nitrogen and heated to 140° C. Epichlorohydrin (19.6 grams) was added over a 10 minute period. The combination was cooled to 60° C. and diluted with 125 millimeters of tetrahydrofuran. A solution of 12.5 grams KOH in 15 millimeters of water was then added. The combination was stirred at 60° C. to 64° C. for 2½ hours. It was then diluted with xylene and washed with water. The reactor contents were stripped to a pot temperature of 225° C. at about 2 millimeters of mercury after adding 2 grams of sodium carbonate. The weight of product was 126 grams.

The polymers that may be conveniently protected by the compounds described herein are oxidizable vulcanized and unvulcanized polymers susceptible to oxygen degradation, such as natural rubber, balata, gutta percha and oxidizable synthetic polymers including those containing carbon to carbon double bonds, such as rubbery diene polymers, both conjugated and nonconjugated. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene. Polyesters can also be stabilized with these compounds.

The phenolic antioxidants of this invention may be used with or without other stabilizers, vulcanizing agents, accelerators or other compounding ingredients. In order to effectively stabilize polymers, small proportions of one or more of the phenolic antioxidants in accordance with this invention are added to the polymer in a customary antioxidant amount which may vary somewhat depending upon the type and requirements of the polymers to be produced. The compounds of this invention are useful in protecting polymer in any form, for example, polymer in latex form, unvulcanized polymer and vulcanized polymer.

The method of addition of the antioxidant to the polymer is not critical. It may be added by any of the conventional means such as by adding to a polymer latex, milling on an open mill or by internal mixing. When the stabilizers of this invention are employed to stabilize the cis-1,4 polyisoprene or cis-1,4 polybutadiene rubbers as described above, a convenient method of incorporation consists of adding the stabilizers to the inert organic solvent in which these polymers are normally prepared after the polymerization of the monomers is essentially complete.

Normally from about 0.001 part to about 5.0 parts of the antioxidant by weight based on the weight of the polymer can be used, although the precise amount of these effective stabilizers which is to be employed will depend somewhat on the nature of the polymer and the severity of the deteriorating conditions to which the polymer is to be exposed. In unsaturated polymers such as those made from conjugated dienes, e.g., rubbery butadiene/styrene polymers, the amount of antioxidant necessary is greater than that required by saturated polymers such as polyethylene. It has been found that an effective antioxidant amount of the disclosed stabilizer in polymers will generally range from about 0.05 part to about 5.0 parts by weight or higher based on 100 parts by weight of the polymer although it is commonly preferred to use from about 0.5 part to about 2.0 parts by weight based on 100 parts by weight of the polymer in most instances where conjugated diene polymers are being stabilized. The above limits are not limiting, but are merely intended to be guidelines.

The following data illustrates, but does not limit, the use of the compounds of the present invention as antioxidants.

SBR 1006, a butadiene/styrene copolymer was stabilized with 1.0 part of various phenolic compounds of the present invention. Oxygen absorption measurements were made at 100° C., the time to a given percent absorption being determined. The results are listed below.

Table 1

| Antioxidant | Hours to Absorb 1.0% O$_2$ |
| --- | --- |
| Example I | 1009 |
| Example II | 325 |
| None | <20 |

Table 2

| Antioxidant | Hours to Absorb 1.0% O$_2$ |
| --- | --- |
| Example I | 957 |
| 2,6-ditertiary butyl-4-(2-hydroxy-2-phenylethylthio)phenol | 340 |

Table 3

| Antioxidant | Hours to Absorb 1.0% O$_2$ in SBR 1006 |
| --- | --- |
| 4-(2-hydroxy-1-propylthio)phenol | 244 |
| 2,6-ditertiary butyl-4-(2-hydroxyethylthio)phenol | 312 |
| 2,6-ditertiary butyl-4-(2-hydroxy-1-propylthio)phenol | 328 |
| 2,6-ditertiary butyl-4-(2-hydroxy-2-phenylethylthio)phenol | 336 |
| 4-(2-hydroxy-2-phenylethylthio)phenol | 880 |
| 1,4-bis-[3-(4-hydroxyphenylthio)-2-hydroxyproxy]butane[1] | 418 |
| 1,4-bis-[3-(3,5-ditertiary butyl-4-hydroxyphenylthio)-2-hydroxypropoxy]butane | 269 |
| 1,3-bis-(3,5-ditertiary butyl-4-hydroxyphenylthio) 2-hydroxypropane | 324 |

[1]Reaction product of 1,4-butandiol diglycidyl ether and 4-(thiol)phenol and believed to contain a major portion of the recited compound.
[2]Reaction product of 1,4-butandiol diglycidyl ether and 2,6-ditertiarybutyl-4-(thiol)phenol and believed to contain a major portion of the recited compound.

The data in Tables 1 to 3 illustrate the effectiveness of the present compound as antioxidants.

All of the phenolic stabilizers described earlier herein can be substituted in the previous working examples to effectively stabilize any of the polymers previously described herein.

The phenolic antioxidants of this invention are relatively non-discoloring antioxidants either before or after aging.

The polymers stabilized by the compounds of the present invention can be used in their same conventional manner. For example, those that are used as tread stocks for tires or in industrial products such as hoses can still be used in such a manner. In fact, to the extent that the antioxidants improve the performance of these rubbers, they can be used under more severe operating conditions.

An example of an unsaturated compound of the present invention is 4-(2-hydroxy-3-butenylthio)phenol.

While certain representative embodiments and details have been shown for the purpose of illustrating the invention, it will be apparent to those skilled in this art that various changes and modifications may be made therein without departing from the spirit or scope of the invention.

I claim:

1. A conjugated diene polymer susceptible to oxidative degradation having incorporated therein a stabilizing amount of a compound having the following structural formula:

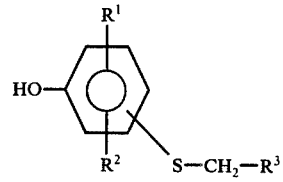

wherein $R^1$ and $R^2$ are selected from the group consisting of hydrogen and hydrocarbon radicals containing 1 to 12 carbon atoms, $R^3$ is a monohydroxy or dihydroxy substituted radical containing 1 to 11 carbon atoms, at least one carbon atom of which is a part of a noncyclic aliphatic portion of the radical, the aliphatic portion of $R^3$ containing the hydroxy substitution, with the proviso that when $R^3$ contains 2 hydroxy substituents the substituents are located on different carbon atoms, and wherein the thio radical is attached to the phenolic ring in a position ortho or para to the hydroxy group.

2. The polymer according to claim 1 wherein $R^1$ and $R^2$ are selected from the group consisting of hydrogen and tertiary alkyl radicals having 4 to 9 carbon atoms and are located in the positions ortho to the hydroxy group, and wherein the thio group is in a position para to the hydroxy groups wherein $R^3$ has the structural formula

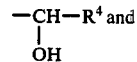

wherein $R^4$ is selected from the group consisting of, methyl and phenyl.

3. The polymer according to claim 2 wherein the compound is selected from the group consisting of 4-(2-hydroxy-2-phenylethylthio)phenol, 2,6-ditertiary butyl-4-(2-hydroxyethylthio)phenol and 2,6-ditertiary butyl-4-(2-hydroxypropylthio)phenol.

4. The polymer according to claim 1 wherein when $n$ is 1, $R^3$ has the structure

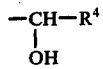

wherein $R^4$ is phenyl.

5. The conjugated diene polymer of claim 1 wherein the polymer is a copolymer of a conjugated 1,3-diene and a monomer selected from the group consisting of styrene and acrylonitrile.

6. The conjugated diene polymer of claim 1 wherein $R^1$ and $R^2$ are hydrogen.

7. A compound having the following structural formula

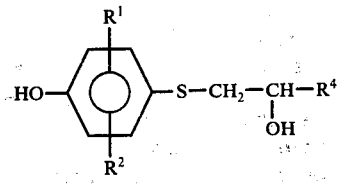

wherein $R^1$ and $R^2$ are selected from the group consisting of hydrogen and hydrocarbon radicals containing 1 to 12 carbon atoms and wherein $R^4$ is selected from the group consisting of hydrogen, methyl and phenyl with the proviso that when $R^4$ is hydrogen $R^1$ and $R^2$ are hydrocarbon radicals containing 1 to 12 carbon atoms.

8. The compound according to claim 7 wherein $R^1$ to $R^2$ are selected from the group consisting of hydrogen and tertiary alkyl radicals having 4 to 9 carbon atoms, being located in the positions ortho to the phenolic hydroxy group, wherein the thio group is in a position para to the phenolic hydroxy group and wherein $R^4$ is phenyl.

9. The compound according to claim 7 wherein $R^1$ and $R^2$ are hydrogen.

* * * * *